United States Patent [19]

Zealear et al.

[11] Patent Number: 4,817,628

[45] Date of Patent: Apr. 4, 1989

[54] SYSTEM AND METHOD FOR EVALUATING NEUROLOGICAL FUNCTION CONTROLLING MUSCULAR MOVEMENTS

[75] Inventors: David L. Zealear, 1061 W. Hollywood #2A, Chicago, Ill. 60660; Alan R. Gibson, Phoenix, Ariz.

[73] Assignee: David L. Zealear, Nashville, Tenn.

[21] Appl. No.: 789,847

[22] Filed: Oct. 18, 1985

[51] Int. Cl.$^4$ ............................................. A61B 15/05
[52] U.S. Cl. .................................... 128/741; 128/643; 128/774; 128/782
[58] Field of Search ........ 128/639, 640, 643, 733–734, 128/741, 744, 774, 777, 782; 73/514; 324/162

[56] References Cited

U.S. PATENT DOCUMENTS

| | | | |
|---|---|---|---|
| 2,580,628 | 1/1952 | Welsch | 128/643 |
| 3,200,814 | 8/1965 | Taylor et al. | |
| 3,320,947 | 5/1967 | Knoll | 128/741 |
| 3,351,880 | 11/1967 | Wilner | 338/6 |
| 3,364,929 | 1/1968 | Ide et al. | 128/741 |
| 3,534,733 | 10/1970 | Phipps | 128/643 |
| 3,557,627 | 1/1971 | Kugath et al. | 73/514 |
| 3,616,698 | 11/1971 | Corey et al. | 73/514 |
| 3,658,054 | 4/1972 | Iberall | |
| 3,664,329 | 5/1972 | Naylor | 128/741 |
| 3,783,865 | 1/1974 | Ricketts | 128/643 |
| 3,785,368 | 1/1974 | McCarthy et al. | 128/639 |
| 3,815,427 | 6/1974 | Gladstone | 73/514 X |
| 3,830,226 | 8/1974 | Staub et al. | 128/741 |
| 3,898,983 | 8/1975 | Elam | 128/741 |
| 4,027,535 | 6/1977 | Swanson | 73/514 X |
| 4,031,883 | 6/1977 | Fehmi et al. | 128/733 X |
| 4,044,870 | 12/1977 | Dumitrescu et al. | 128/741 |
| 4,088,125 | 5/1978 | Forgione et al. | 128/741 X |
| 4,095,551 | 6/1978 | Paul et al. | 73/514 X |
| 4,166,452 | 9/1979 | Generales, Jr. | 128/741 |
| 4,174,706 | 11/1979 | Jankelson et al. | 128/741 |
| 4,198,990 | 4/1980 | Higgins et al. | 128/782 |
| 4,217,908 | 8/1980 | Staver | 128/643 |
| 4,236,528 | 12/1980 | Stanec et al. | 128/741 |
| 4,291,705 | 9/1981 | Severinghaus et al. | 128/733 |
| 4,344,441 | 8/1982 | Radke | 128/733 |
| 4,359,724 | 11/1982 | Zimmerman et al. | 128/733 X |
| 4,387,723 | 6/1983 | Atlee, III et al. | 128/734 |

(List continued on next page.)

FOREIGN PATENT DOCUMENTS 0041807 12/1981 European Pat. Off. .

OTHER PUBLICATIONS

Fiore et al.; "A Microcomputer-Based Neuromuscular Blockade Monitor", *IEEE Trans. on Biomed. Engr.*, vol. BME-28, No. 11, 11-1981, pp. 775-783.

(List continued on next page.)

*Primary Examiner*—Kyle L. Howell
*Assistant Examiner*—Angela D. Sykes
*Attorney, Agent, or Firm*—Banner, Birch, McKie & Beckett

[57] ABSTRACT

A system for evaluating nervous system function of a subject including generally an accelerometer sensor, a stimulus electrode assembly, and a portable device to which the sensor and electrode assembly are connected. The sensor measures the magnitude of the (stimulus evoked) movement of a body part of the subject along at least one axis of three dimensional space. The device contains electrical circuits for processing data from the sensor, generating stimuli to the electrode assembly, and timing both the extraction of sensor information and the delivery of stimuli. The sensor has a suction chamber for attaching the sensor to the desired body part site by static suction. To evaluate the nervous system function the magnitude of the monitored sensed (acceleration) movement is compared with a control value. When the nervous system being evaluated is the peripheral nerve of one side of the face, the control value can be determined by evoking and measuring movement on the opposite side of the face. For this embodiment, two pairs of electrodes are attached to a headband which holds them simultaneously against opposite sides of the face and a switch communicates the desired pair with the portable device.

51 Claims, 6 Drawing Sheets

U.S. PATENT DOCUMENTS

| | | | |
|---|---|---|---|
| 4,437,473 | 3/1984 | Mollan | 128/773 |
| 4,444,205 | 4/1984 | Jackson | 128/782 |
| 4,448,203 | 5/1984 | Williamson et al. | 128/733 |
| 4,488,445 | 12/1984 | Aske | 73/514 X |
| 4,492,233 | 1/1985 | Petrofsky et al. | 128/421 |
| 4,503,863 | 3/1985 | Katims | 128/741 |
| 4,515,168 | 5/1985 | Chester et al. | 128/741 |
| 4,540,002 | 9/1985 | Atlas | 128/734 |
| 4,595,018 | 6/1986 | Rantala | 128/733 |
| 4,653,001 | 3/1987 | Semenon et al. | 128/745 X |

OTHER PUBLICATIONS

Pavlov et al., "Neuromuscular Block Indicator"; *Biomed. Engr.*, vol. 13, No. 4, 3–1980, pp. 205–207.

"Grass Accelerometer for Parkinsonism".

"Kistler Piezo Instrumentation Accelerometers".

"WR Medical Electronics Co.–Nerve Monitors".

Lance, James W., et al., "Action Tremor and the Cogwheel Phenomenon in Parkinson's Disease", *Brain J.* 86:95–110, 1963.

May, M., Klein, S. R., Blumenthal, F.; Evoked Electromyography and Idiopathic Facial Paralysis, *Otolaryngol.–Head & Neck Surg.* 91:678–685, 1983.

Hughes, G. B., Josey, A.F., Glasscock, M. E., Jackson, C. G., Ray, W. A., Sismanis, A.: Clinical electroneurography: statistical analysis of controlled measurements in twenty-two normal subjects. The Laryngoscope 19:1834–1846, 1981.

Cambell, E. D., Hickey, R. P., Nixon, K. H., and A. T. Richardson: Value of Nerve-Excitability Measurements in Prognosis of Facial Palsy, *Brit. Med. J.*, 2:7–10, 1962.

Burke, R. E. Rudomin, P., and F. E. Zajac, III: The Effect of Activation History on Tension Production by Individual Muscle Units, *Brain Res.* 109:515–529, 1976.

Gantz, B. J., Holliday, M. Gmuer, A. A., and U. Fisch: Electroneurographic Evaluation of the Facial Nerve, Method and Technical Problems, *Ann. Otol. Rhinol. Laryngol.* 93:394–398, 1984.

Hughes, G. B., Nodar, R. H., and G. W. Williams: Analaysis of Test–Retest Variability in Facial Electroneurography, *Otolaryngol.–Head & Neck Surg.* 91:290–293, 1983.

May M., Harvey J. E., Marovits W. F., and M. Stroud: The Prognostic Accuracy of the Maximal Stimulation Test Compared with that of the Nerve Excitability Test in Bell's Palsy, *Laryngoscope* 81:931–938, 1971.

Fisch U.: Diagnostic Studies on Idiopathic Facial Palsy, In *Proceedings of Shambaugh Fifth International Workshop on Middle Ear Microsurgery and Fluctuant Hearing Loss*, Eds. Shambaugh, G. E. and J. J. Shea, The Stroke Pub., Inc. Huntsville, Ala., 1977.

Esslen, E.: Electromyography and Electroneuronography, *In Facial Nerve Surgery*, Ed. U. Fisch, Aesculapius Publishing Co., Birmingham, Ala., 1977, (93–100).

Fisch, U.: Facial Paralysis in Fractures of the Petrous Bone, Laryngoscope 84:2141–2154, 1974.

Fisch, U.: Maximal Nerve Excitability Testing vs Electroneuronography, *Arch Otolaryngol*, 106:352–357, 1980.

Kartush, J. M., Lilly, D. J., Kemink, J. L.: Facial Electroneurography: Clinical and Experimental Investigations, Otolaryngol–Head & Neck Surg. 93:516–523, 1983.

"Experimental Method for Determining the 2-Dimensional Mechanical Properties of Living Human Skin", T. Cook et al., Medical and Biological Engineering and Computing, Jul. 1977.

"Subminiature Three-Directional Accelerometer: An Application of Semi-Conductor Strain Gages", Chiku et al., ISA Transactions, vol. 9, No. 2, 1970.

Fisch, U.: Prognostic Value of Electrical Tests in Acute Facial Paralysis, *Amer. J. Otol.*, 5:494–498, 1984.

Zealear, D. L. and Kurago, K.: Facial Nerve Recording from the Eardrum: A Possible Method for Evaluating Idiopathic Facial Nerve Paralysis, *Otolaryngology Heat & Neck Surgery*, 93:474–481, Aug. 1985.

Pansky, B. and E. L. House, *Review of Gross Anatomy Second Edition*, pp. 20–23.

SYSTEM AND METHOD FOR EVALUATING NEUROLOGICAL FUNCTION CONTROLLING MUSCULAR MOVEMENTS

BACKGROUND AND OBJECTS OF THE INVENTION

The present invention relates to devices and methods for evaluating neurological function controlling muscular movements and, more particularly, for evaluating peripheral nerve function.

A peripheral motor nerve is composed of many nerve fibers which transmit or conduct electrical signals from the central nervous system to the muscles they control. Each nerve fiber branches at its termination and contacts as many as 200–300 muscle fibers, so that when a signal arrives at the terminals of a nerve fiber the muscle fibers also become electrically active. Muscle fibers are unusual and are distinguished from nerve fibers, however, in that once they are electrically active they also contract and generate force to move part of the body. It is common knowledge that very complicated sequential movements of one or more body parts can be produced (such as playing the piano) if the central nervous system can recruit the proper combination of nerve fibers for each movement in the sequence.

In many instances central nervous system command signals are generated but their conduction down nerve fibers is disturbed en route because of a pathological change or lesion in the peripheral nerve. In the initial stage of a lesion, signal conduction becomes less efficient so that there is a slowing of conduction in the nerve fibers affected. If the lesion intensifies, signal conduction may become blocked in these nerve fibers. Their corresponding muscle fibers can no longer be made to contract and the patient has a partial paralysis termed "a paresis". A lesion can intensify to block the entire nerve thereby producing a total paralysis.

In cases where a peripheral nerve lesion is suspected, it is important for the physician to test the nerve to determine if and to what extent signal conduction has been compromised. This information is not only important in predicting the outcome in a patient's paralysis (i.e. whether the patient will eventually recover from the paralysis or not) but also in deciding whether a particular form of treatment, such as surgery, should be advised. The most common method currently available to assess nerve signal conduction is the "nerve conduction velocity" test. Pairs of stimulus and recording electrodes are placed on the skin overlying the nerve on each side of the nerve lesion. When a stimulus is applied by passing electricity through the skin, nerve fibers are activated and a volley of signals (termed a "compound action potential") is conducted down the nerve through the lesion towards the recording electrodes. When the action potential reaches the recording electrodes, the voltage change detected by the electrodes can be amplified and displayed on an oscilloscope. The potential actually represents a compound voltage of all nerve fiber signals that made it through the lesion. The physician notes on the oscilloscope the time required for the potential to travel from the stimulus electrodes to the recording electrodes. By measuring the distance between the electrodes, he can calculate the average conduction velocity of the potential and compare it to normal values to gain some appreciation as to whether the lesion caused a slowing of signal conduction. The physician might also note that the recorded potential is subnormal in size suggesting that some nerve fiber signals were blocked at the lesion site. Unfortunately, the amplitude of a potential that can be recorded from a nerve through the skin is very small (approximately ten microvolts), so that decreases stemming from signal blocking are difficult to detect. This problem is compounded by the fact that slight changes in the recording electrode position can also cause significant changes in the size of the recorded potential. Thus, the method lacks adequate sensitivity and accuracy for assessing signal blocking that occurs with intensification of a nerve lesion.

A modification of the method which attempts to give a better assessment of signal blocking at a lesion is called "evoked electromyography". Evoked electromyography is most commonly utilized for evaluating facial nerve function (many physicians call the test "electroneurography" when used in this application). With this technique recording electrodes are placed on the skin overlying some of the muscle fibers that are controlled by the nerve rather than on the skin overlying the nerve. Following activation of the nerve by stimulation, these muscle fibers also become electrically active. The compound voltage from muscle fibers or "electromyographic potential" can be detected by the recording electrodes, amplified, and displayed on an oscilloscope. The physician can determine if the recorded response is abnormal in either latency (time delay before response) or in amplitude, indicating nerve signal slowing or blocking, respectively. Unfortunately, this technique also has severe limitations with respect to sensitivity and accuracy. Although the potential recorded from muscle is larger than that recorded from nerve in a normal person, the electromyographic potential recorded from most patients with nerve signal blocks is too small to be accurately measured. The recorded data must first be fed into a signal averager in order to obtain sufficient signal to noise ratio to measure the response. Very few physicians employ this test because of the complexity and cost required in using a signal averager. The test is also inaccurate. Slight changes in the electrode position produce changes in response amplitude or error that are greater than 15% and as large as 100%. The method has another limitation in that only those nerve fibers controlling muscle fibers in the vicinity of the recording electrodes can be assessed for damage. Nerve fibers controlling muscle fibers outside this region may also become damaged by a lesion, but no change in the recorded potential will be observed. Thus, the method represents a sampling technique and can not assess the status of the entire nerve.

The primary objects of the present invention are to provide a method and a device for evaluating the functions of regions of the nervous system, particularly peripheral nerves, that control muscular movements, using a method and device which is simpler, more sensitive, more accurate, less costly, and safer than prior methods and devices.

Other objects and advantages of the present invention will become more apparent to those persons having ordinary skill in the art to which the present invention pertains from the following description taken in conjunction with the accompanying drawings.

BRIEF DESCRIPTION OF THE PREFERRED EMBODIMENT

Since there are problems in measuring the electrical activity of nerve or muscle following nerve stimulation as described previously, the present method has been developed for assessing nerve function by measuring the mechanical activity evoked by the stimulation. Following nerve stimulation, a movement or "jerk" of a body part occurs because of muscular activity. The acceleration associated with this movement can be measured simply by affixing a small accelerometer sensor with negligible mass to the body part. Since acceleration varies directly with the force generated in moving the body part (as long as its mass remains constant), the acceleration measured by the sensor is an index of force. The force generated, in turn, is directly related to the number of nerve fiber signals that reached the muscles following nerve stimulation. In a patient with a developing lesion, a decrease will be observed in the measured acceleration or force of an evoked movement as nerve fiber signals become blocked by the lesion. The percent decrease in force from normal should be, in fact, related to the percent of blocked fibers by the lesion. Slowing of nerve fiber signal conduction can also be determined with this method by measuring the latency of the force response following nerve stimulation.

DETAILED DESCRIPTION OF THE PREFERRED EMBODIMENT

Figure 1:
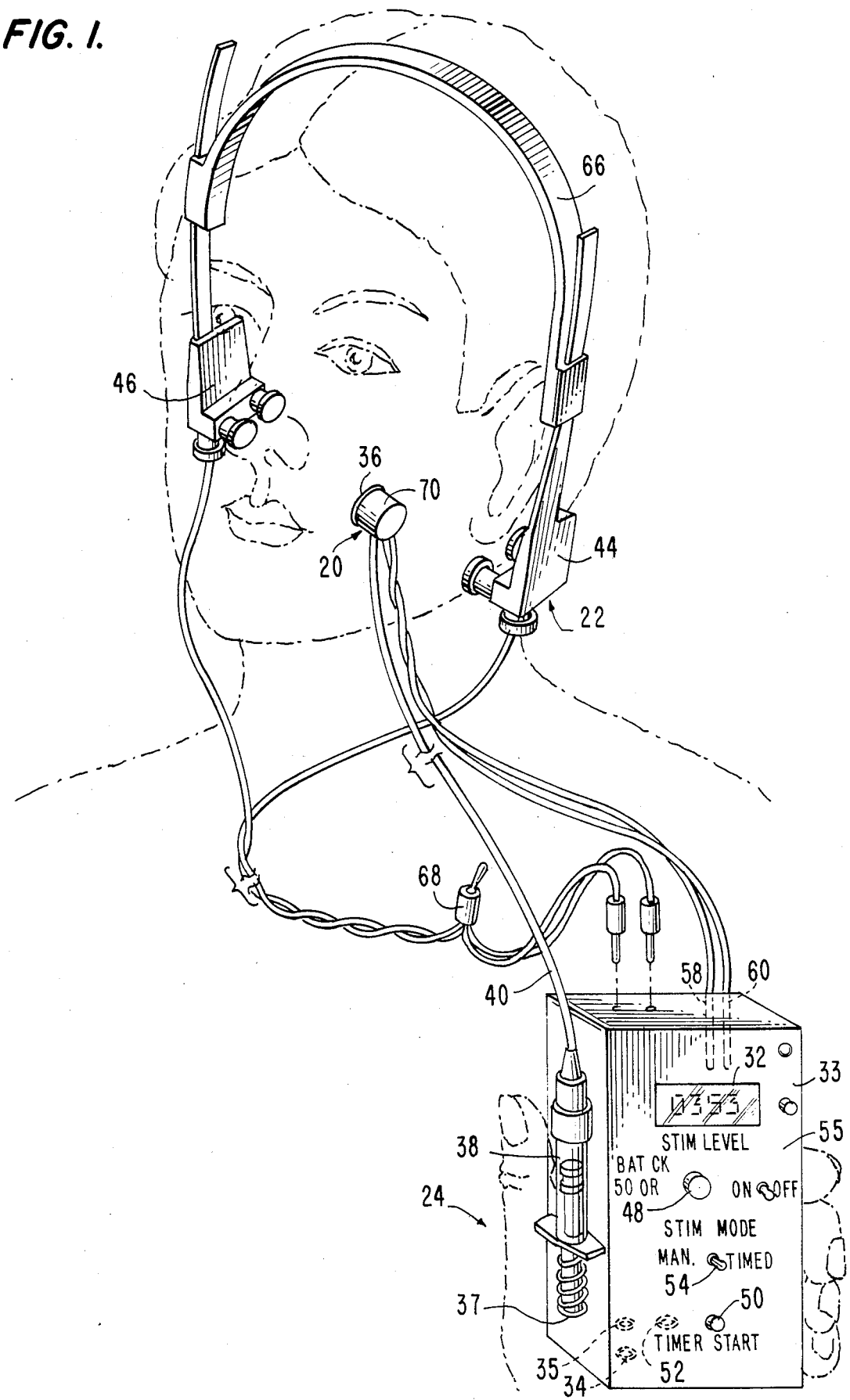
FIG. 1 is a perspective view of a system of the present invention.
Figure 6:
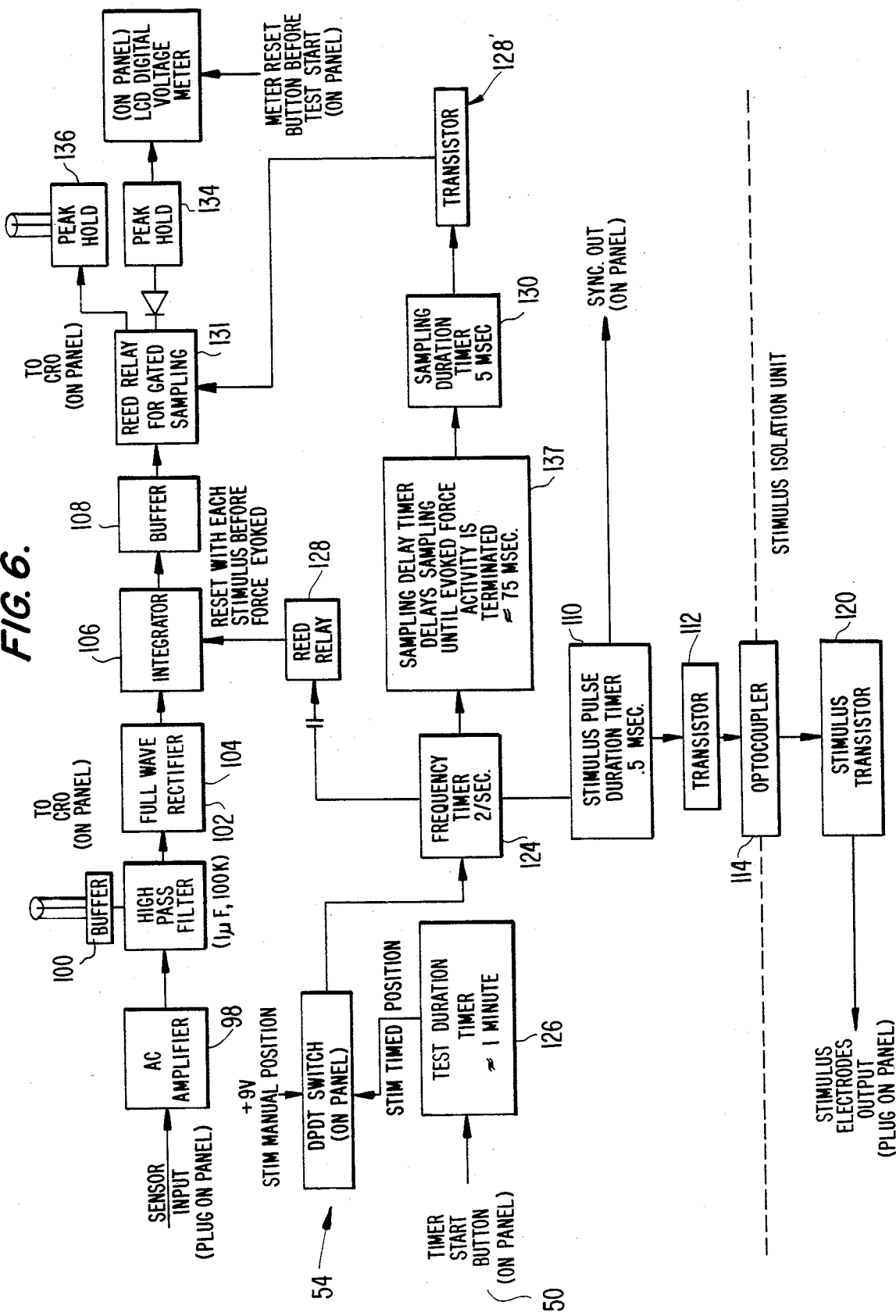
FIG. 6 is a block diagram illustrating the operation of the system of FIG. 1.
Figure 7:
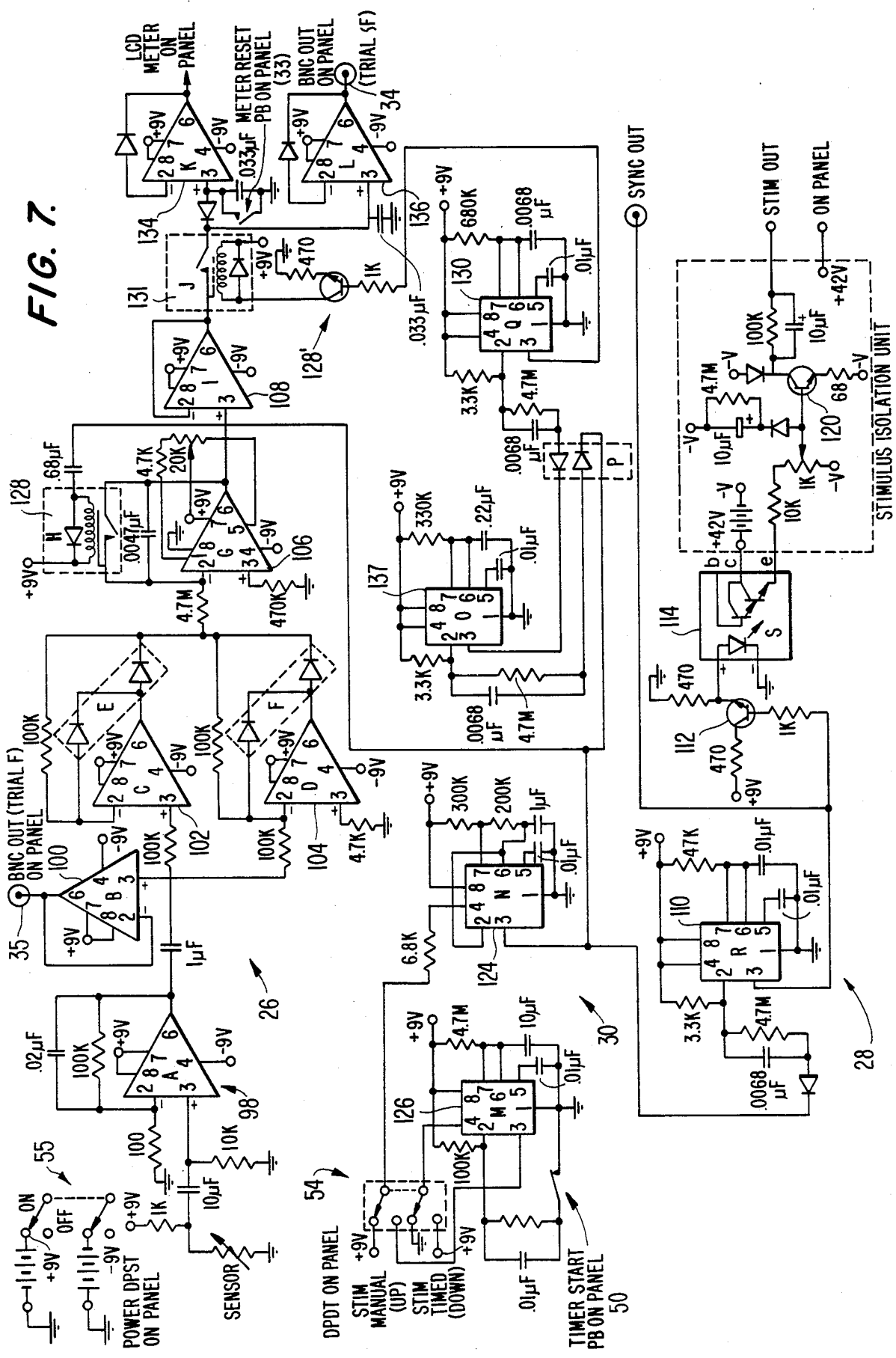
FIG. 7 is an electrical schematic for the system of FIG. 1.

Referring to FIG. 1, the basic components of the preferred embodiment of the subject invention include an accelerometer sensor 20 for measuring evoked movement, a stimulus electrode assembly 22 for activating a nerve, and a portable DC powered device 24. Device 24 contains three circuits, as shown in FIGS. 6 and 7—a sensor circuit 26 for processing sensor information, a stimulus circuit 28 for delivering stimuli, and a timing circuit 30 for timing both the delivery of stimuli and extraction of processed sensor information. Device 24 works in either an automatic or manual mode and test results are read out on its LCD meter 32. Output plugs 34, 35 are also included to provide the option for analogue waveforms to be viewed on an oscilloscope or to be strip chart recorded.

The basic steps to determine the largest integrated force that can be evoked over a time interval of one minute are as follows: (1) accelerometer sensor 20 is held by placing O' ring 36 at a specified site on the body part supplied by the nerve; (2) the spring-biased plunger 37 of the suction syringe 38, which will releasably clamp onto the side of device 24, is depressed and then released to create suction, via polyethylene suction tube 40, in the external compartment 42 of sensor 20, thereby affixing it to the skin; (3) skin at a specified site overlying the nerve is wiped with a degreasing agent (e.g. alcohol); (4) a pair of stimulus electrodes 44, 46 is placed at the site; (5) the stimulus intensity knob 48 on device 24 is adjusted to a value known to deliver sufficient current to activate all functional nerve fibers in the nerve; (6) the "start" button 50 of device 24 is depressed; and (7) the readout on LCD meter 32 is noted and recorded. The user compares the value obtained to a normal value for the nerve and can express the value as a percent of normal function if desired. Before depressing "start" button 50, if the user makes a connection between the "trial integrated force" plug 34 and an external device displaying voltage as a function of time (e.g. oscilloscope, strip chart recorder), the integrated force evoked with each stimulus during the test can be monitored. Alternatively, the user can monitor the force waveform evoked with each stimulus by connecting the "trial force" plug 35 to the external device. There is also a "sync out" plug 52 provided to trigger the external device (e.g. oscilloscope) during each stimulus. Finally, the user can specify his own time interval over which a test will be conducted. Instead of depressing "start" button 50, the user flips the DPDT switch 54 on the panel of the device to the "stim manual" position to start the test and flips it back to the "stim timed" position to stop the test.

Device 24 is DC powered and enclosed in a portable box which can be held in one hand, as best shown in FIG. 1. The box has external plugs 58, 60 to make input connections to the sensor 20 and output connections to a pair of stimulus electrodes 44, 46. Two types of stimulus electrodes are available. One type is of a standard bipolar configuration and can be used for activating most nerves of the body simply by holding the electrodes on the skin. The second type shown generally at 22 is a novel design and can be used for activating either the left or right facial nerve. The facial nerve stimulus electrodes of the second type are novel in two respects. First, they are attached to an adjustable headband 66 which provides a convenient means for holding them on the skin overlying the facial nerves. These electrodes are also particularly useful when performing electromyography of the facial nerve (electroneuography). If the method is performed using the standard type of electrodes, the electrodes must be held against the skin. Since the technician must use his other hand to hold the recording electrodes, he has no free hand to run the signal averager, and thus a second technician must be present to perform this function. When using the subject stimulus electrodes 22 the first technician has a free hand to manipulate the averager, so that the aid, or even presence, of a second technician is not required. These electrodes are also more convenient when performing evoked accelerometry, since the electrodes allow both hands of the technician to be free for other tasks, inasmuch as it is not necessary to hold the sensor on the face.

The second novel aspect of this electrode design is that it incorporates two pairs of electrodes 44, 46 and a switch 68 to direct the stimulation to either facial nerve. Pairs of felt-lined electrodes 44, 46 are positioned at both ends of headband 66, so that when band 66 is put on the head the pairs of electrodes 44, 46 lie against the skin overlying the facial nerves as they exit the skull. As illustrated in FIG. 1, each pair of electrodes is positioned so that one electrode is in front of the ear lobe and the other one is behind it. It is further within the scope of the present invention to saturate the electrodes with saline for effective transfer of current. Stimuli generated by device 24 can then be directed to either pair of electrodes by flicking switch 68. It is thus not necessary to move a single pair of electrodes from one side of the face to the other. As will be discussed in greater detail later, the present invention provides that both the normal and damaged nerve can be tested in a patient so that their respective nerve functions can be compared. It is also within the scope of the invention to use static suction, as described later for the sensor 20, to hold stimulus electrodes 44, 46 against the skin.

Figure 2:
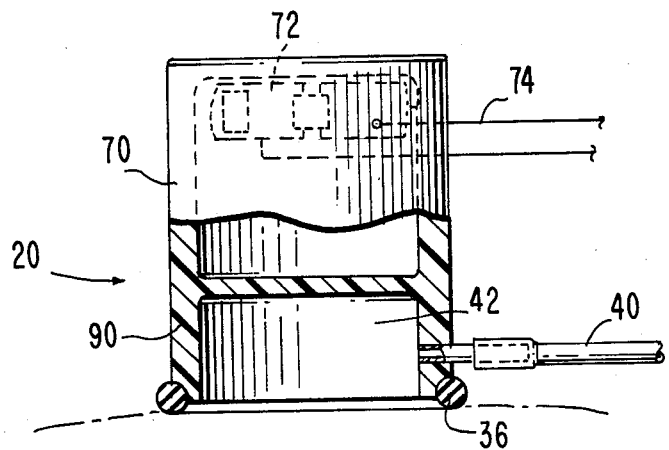
FIG. 2 is an enlarged side elevational view of the sensor of FIG. 1 having portions thereof broken away.
Figure 3:
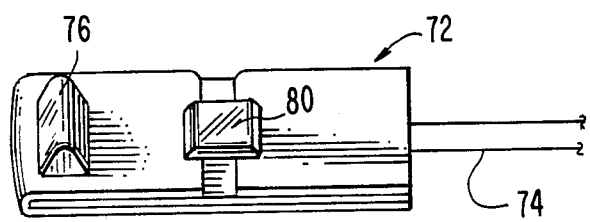
FIG. 3 is an enlarged view of the filament of the sensor of FIG. 2.
Figure 4:
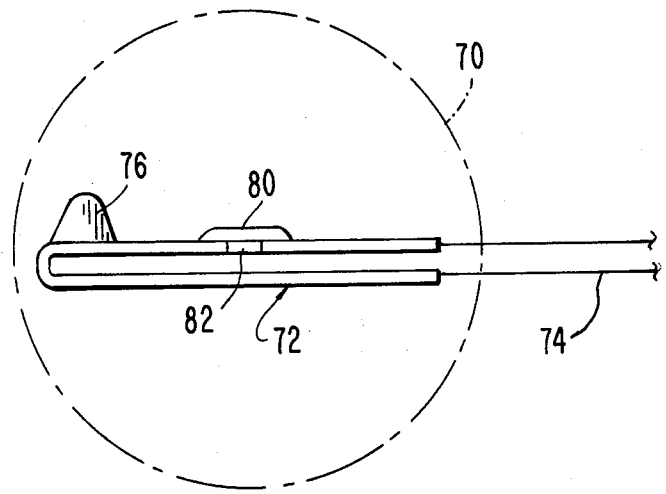
FIG. 4 is a top view of the filament of FIG. 3.
Figure 5:
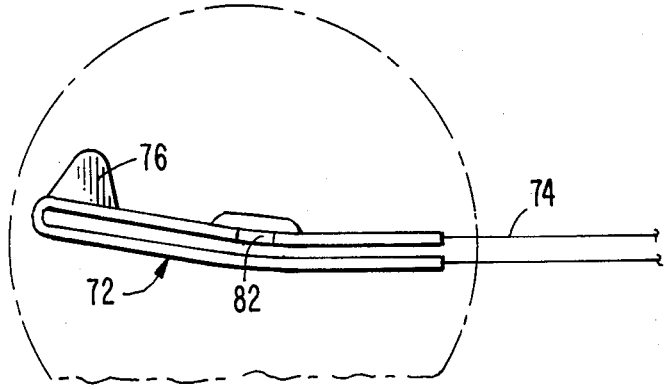
FIG. 5 is a view similar to FIG. 4 illustrating the filament in its flexed condition.

As shown in FIG. 2, sensor 20 is a single axis type of accelerometer encased in a barrel housing 70 approximately 5 mm in diameter and 5 mm in length. Sensor 20 is configured from a filament 72 as shown and such is as manufactured by Endevco (Pixie transducer, model range 8101,1 U.S. Pat. Nos. 3,351,880 and 3,501,732). Lead wires 74 are then soldered to one end of the filament 72, a weight 76 of known mass is attached to the other end, and the lead wire end anchored inside sensor housing 70. When the skin to which the housing 70 is attached moves, the housing 70 and lead wire end 74 of the filament are accelerated. As illustrated in FIGS. 4 and 5, filament 72 flexes when accelerating the suspended weight 76 on the other end, leading to elongation or compression of the piezoresistive crystal 80. Since the crystal distortion causes a change in its resistance which is proportional to the distorting force, the resistance change observed is a measure of the force which produced the acceleration of weight 76.

The sensor filament 72 measures the force of a movement as follows. First note that in FIGS. 4 and 5 there is an air gap 82 illustrated below piezoresistive crystal 80. When the body part moves sensor housing 70 the anchored end of the filament also moves. The movement causes flexion of the filament 72, with much of the flexion occurring at its weak point, that is, below air gap 82. The flexion, in turn, causes compression of the piezoresistive crystal 80 and a change in its resistance. This resistance change is measured and is an index of the magnitude of the force that produced the movement. That is, a larger body part force and movement will result in a proportionally larger filament flexion, crystal compression and measured resistance change. It can also be appreciated that the actual amount of flexion that occurs with a movement depends upon the size of weight 76 that is attached to the free end of the filament 72. For a given body part force and movement, the amount of flexion will increase if a larger weight 76 is attached. That is, the sensitivity of the filament sensor can be increased by attaching a larger weight. Weights of approximately 300 milligrams can be used to obtain adequate filament sensitivity. Larger weights could be used, but as can be appreciated there is a limit in the size of weight that can be used, since extremely large weights make filament 72 more susceptible to breakage. To summarize, the filament resistance change that is measured is proportional to the body part force producing the movement times the mass of the sensor weight.

Methods which do not provide for a secure attachment of sensor 20 to skin should preferably not be used (e.g. taping, tieing), because errors in measuring acceleration will undoubtably be introduced. Adhesives, however, can provide for a secure attachment but once they are applied it is not as easy to relocate the sensor as it is when using suction. Adhesives though might be useful and possibly preferable to suction in applications where acceleration must be measured over a long period of time, such as an hour or so, since prolonged suction can cause damage to skin vessels. In particular, commercially available rubber disks (not shown) with adhesive on both sides and backed with waxed paper can be used to attach the sensor. One side of the disk can be stuck to the sensor and the other side to the skin, after removing the wax paper from each side.

Measuring the force generated by the face along one axis is sufficient to give consistent and accurate information regarding the number of incoming nerve fiber signals. It may be necessary though to use a biaxial or triaxial accelerometer to accurately assess nerve function of other peripheral nerves. In particular, it may be necessary to measure the magnitude of the actual force vector in three-dimensional space. The triaxial type can measure the component of the actual force vector forces along three orthogonal axes. The magnitude of the actual force vector can be obtained by squaring the component forces, summing these squared values, and square-rooting the sum. IC chips are available that square, sum, and square root, so the present device can be easily modified to incorporate these chips if it becomes necessary to use one of the more sophisticated types of accelerometers in a particular application. Each of the three types of accelerometers are commercially available.

Figure 8:
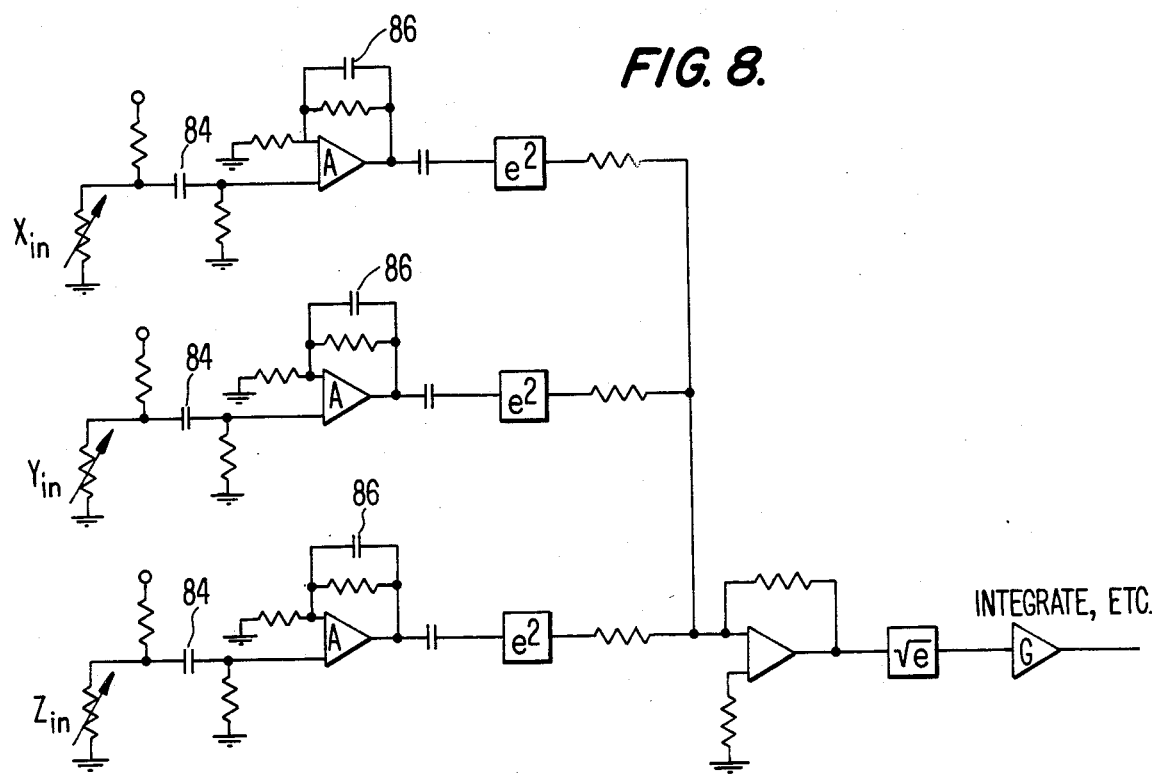
FIG. 8 is an electrical schematic illustrating a variation of the sensor circuit portion of the schematic of FIG. 7.

The sensor circuit would be modified as shown in FIG. 8 where a triaxial accelerometer is used. Note that there is no need to rectify after op-amps "A" as before (see FIG. 7), since squaring makes all negative component vectors positive before summing. Other possible modifications include changing the values of high pass filters 84 or low pass filters 86 depending upon the particular frequency response of the force that is evoked. Another modification which may be necessary is to change the time delay before sampling (determined by timer "0") in instances where the latency or duration of the evoked force vary significantly from that observed for the face response. The delay can be changed simply by substituting another value of the 330K resistor.

The preferred single axis accelerometer has a flange 90 extending from one end forming a novel open-ended compartment 42. A rubber O-ring 36 is attached to the rim of flange 90. The end of polyethylene tube 40 is inserted into compartment 42. Accelerometers having higher sensitivity and less fragility are commercially available, however, and could be used with this device, once equipped with the static suction compartment 42. The other end of polyethylene tube 40 is then connected to a spring-loaded syringe 38. When plunger 37 of syringe 38 is depressed compressing the spring, air is driven out of compartment 42. If O-ring 36 is then placed on the skin, compartment 42 is closed. When the syringe plunger 37 is then released, it springs back creating a vacuum in compartment 42. This method of creating static suction is an efficient and simple means for attaching accelerometer sensor 20 to the subject's skin at the desired location.

Device 24 incorporates three different circuits 26, 28, 30 as diagrammed in FIG. 7. The first circuit 26 (top of FIG. 1) processes incoming sensor information. The second circuit 28 (bottom of FIG. 7) controls the strength of stimuli that are delivered during the test period. The third circuit 30 (middle of FIG. 7) is a timing circuit which controls the duration of the testing period (the period of time over which stimuli will be delivered), the frequency or rate at which square-wave stimuli will be delivered, and the duration of each square-wave stimulus.

Referring to sensor circuit 26, when the power is on, movements detected by sensor 20 will be continuously decoded by this circuit as analogue voltage signals. That is, movements cause resistance changes in the sensor as previously described. Since the sensor resistance is part of a voltage divider, voltage changes occur reflecting the resistance changes. The voltage signals (force signals) are first filtered by a high pass filter (10 uF×10K). They are then amplified 1000 times by op-amp 98. Next they are filtered by a low pass filter (0.02 uF feedback capacitor on 98). They are high pass filtered again after amplification (1 uF×100K) to get rid of any inherent drift in op-amp 98. These force signals can be monitored directly on an oscilloscope if a connection is made to the buffer op-amp 100. Since the amplified signals can be either positive or negative, they are full-wave rectified by op-amps 102 and 104. Op-amp 102 passes positive signals and op-amp 104 passes inverted negative signals, so that the input to the integrator op-amp 106 is always positive. Integrator op-amp 106 integrates these signals, with a time constant determined by the input resistance (4.7M) and the feedback capacitance (0.0047 uF). The time constant is long enough so that the capacitor will not fully charge by an incoming force signal that is maximum in size. Integrator op-amp 106 is the only one in the circuit equipped with a trim pot (20K) to compensate for drift. However, precise trimming is not necessary in this circuit, because integrated values are rezeroed so frequently (every 500 milliseconds). Since positive signals enter the negative input of op-amp 106, these signals are inverted by 106 after integration and remain negative throughout the rest of the circuit (see LCD meter 32). The polarity is not reverted by the buffer op-amp 108, since this might compromise the isolation of charge stored by the integrator.

Stimulus circuit 28 is driven by the stimulus duration timer 110. It provides a sync out pulse for triggering an external device (CRO) and turns on a transistor 112. Transistor 112, in turn, passes 0.5 millisecond stimulus pulses optically to a Darlington phototransistor in the optocoupler 114. The intensity of the pulses is then controlled by the stimulus isolation unit circuit. This circuit is not only optically isolated by optocoupler 114 but also physically isolated from the rest of the circuit to prevent any possibility of severe electric shock (i.e. when the circuit is connected to an external, AC powered, earth grounded piece of equipment). When the phototransistor is turned on, it supplies a potentiometer with 4.2 volts. The wiper of the potentiometer is controlled by the "stimulus intensity" knob on the front panel of device 24. It determines the amplitude (voltage) of the pulses seen by the base of the stimulus intensity transistor 120. During a pulse, the higher the base voltage setting, the more the transistor is turned on and the larger the current that is drawn into the collector from stimulus electrodes 44, 46 placed on the skin.

There are three other elements in this circuit. First, a parallel RC element (100k, 10 uF) is placed between the collector and the stimulus electrodes as a safety feature. When the circuit is functioning normally, the transistor turns on with incoming pulses, drawing current from the electrodes through the 10 uF capacitor. That is, the 100k resistor is normally shunted. However, if the transistor for some reason becomes damaged and is always turned on, current will only be drawn from the electrodes until the capacitor becomes charged (i.e., for a second or two). After the capacitor is charged, current must pass through the 100K resistor. This resistance value is high and limits the current that can be drawn through the skin to an insignificant level. Second, a rectifier is placed on the collector to −V to prevent damage occurring to the transistor during discharge of the 10 uF capacitor. Third, a parallel RC element (10 uF, 4.7M) in series with a rectifier is placed on the base to −V. This provides for shunting of base current with incoming pulses until the capacitor is charged. The transistor gradually turns on at the start of a test, reaching the predetermined level set by the potentiometer about five seconds later. This prevents a naive subject from being startled by the first few stimulus pulses and allows him sufficient time to get accustomed to the stimulation.

Referring to timer circuit 30 in the middle of the schematic, once the power is turned on by switch 55, if DPDT switch 54 is flipped to the "stim manual" position, +9 V is supplied to the reset pin of frequency timer 124. This timer will put out square wave pulses 350 milliseconds in duration and at a rate of two per second as long as its reset is supplied with 9 V. Frequency timer 124 can also be activated via its reset pin for a set period of one minute by flipping DPDT switch 54 to the "stim timed" mode and depressing "timer start" button 50. The start button triggers the test duration timer 126 to put on a +9 V square wave pulse of one minute duration. When frequency timer 124 is on, its output pulses activate three circuit components synchronously: stimulus duration timer 110, sampling delay timer 137, and integrator reset switch (reed relay 128). These components are activitated on the break of a (frequency timer) pulse (i.e. fall from +9 V to ground). Stimulus duration timer 110 is set to put out a 0.5 milliseconds (+) pulse each time it is activated by an incoming pulse break. The integrator reset switch is closed only momentarily with a pulse break, since it is capacitatively coupled (0.68 uF) to frequency timer 124. It is closed at the beginning of a stimulus pulse and performs the function of discharging the capacitor on integrator op-amp 106, rezeroing its stored value of integrated force. With a frequency timer pulse break (the start of a stimulus pulse), the sampling delay timer 137 also puts out a (+) pulse of set duration (seventy-five milliseconds). This is the period of time it takes for a movement (i.e. force) evoked by a stimulus pulse to be completed. When a delay timer pulse breaks, the break activates the sampling duration timer 130. When timer 130 is activated, it puts out a five millisecond (+) pulse to close reed relay 131. A transistor 128 is inserted in the circuit to actually close the reed relay. During the five milliseconds that the relay is closed, the two peak hold op-amps 134 and 136 can "read" the value of integrated force that is stored on the capacitor of integrator op-amp 106. They actually read the value indirectly through a buffer op-amp 108 which protects the value on the capacitor. The effects timer circuit 30 has on sensor circuit 26 are summarized as follows. The value of integrated force stored on the integrator capacitor is rezeroed at the beginning of each stimulus pulse. Integration of incoming sensor information then proceeds until the next stimulus. Seventy-five milliseconds after a stimulus, the period of time it takes for an evoked movement to be completed, a reed relay 131 is briefly closed so that the peak hold op-amps can read the value of integrated force that was evoked by the stimulus.

In summary, during the period of stimulation, incoming sensor information (electrical analogue of force or acceleration) is amplified, filtered, rectified, and integrated. What is obtained is the integral of force over time. The circuit is designed this way because evoked force multiplied by the time interval of force generation is a better index of nerve activity than is peak force. The integrator is reset or zeroed at the beginning of each stimulus by the frequency timer, so that only the force generated following a single stimulus is integrated and stored until the next stimulus. The value stored on the integrator is protected by a buffer op-amp as shown. Although the filter in sensor circuit 26 can be set to pass a narrow range of frequencies, in particular, the range of frequencies encountered during evoked movement, the filter might also pass force information associated with nonspecific movements that are unrelated to the one that is evoked. That is, when a subject is being tested, he may make involuntary movements that are detected by the sensor. If this information gets through the filter to the integrator, it will add to the value that the integrator stored from the evoked movement. To prevent inaccuracy in the measurement of evoked force, the circuit has two peak hold components that briefly sample the value stored by the integrator shortly after the termination of an evoked movement. The components ignore any further changes in the value due to nonspecific movements (or drift). As shown in FIGS. 6 and 7, a delay timer 137 determines when the sampling will begin following each stimulus and a sample duration timer determines the sampling interval. Sampling is mediated by (closing) a reed relay between the peak hold components and the integrator buffer. The two peak hold components differ in that one has a rectifier on its input. The one without the rectifier holds the value of integrated force resulting from a given stimulus. An external plug allows this information to be displayed on a CRO or strip chart recorder, so that changes in integrated force that occur over the testing period can be appreciated. The peak hold component with the rectifier on its input holds a value of integrated force resulting from a stimulus until some subsequent stimulus produces a larger integrated force. The component then updates its information by storing the larger value. Since the component values are displayed on an LCD digital voltmeter on the face of the device, the updating can be observed as it occurs during testing. At the end of the test period, the maximum integrated force value which could be evoked during the test period remains displayed on the meter until it is reset. The reason the maximum value is of interest is because evoked force increases through a process called "muscle potentiation" during repetitive stimulation until a maximum (fully potentiated) condition is reached. It takes anywhere from a few seconds to a minute of stimulation to reach a fully potentiated state, the time required depending upon the initial state of potentiation. A sufficiently long test period has been chosen (approximately one minute) to assure that each time a subject's nerve is tested the muscles are always in the same state of potentiation (i.e. fully potentiated) so as to minimize intertest error.

With the present device 24 the variability in the readout during repeated testing of one side of a normal subject's face (intertest variability) is less than 5%. The variability in the readout between the two sides of the face (bilateral variability) is generally indistinguishable from the intertest variability. That is, bilateral variability appears to be negligible. Thus, in patients with one-sided paralysis (the most common clinical situation), the unafflicted side can be tested to obtain a value for a normal response. If after having tested the paralyzed side the readout is less than 95% of this value, the nerve should be considered damaged. Furthermore, the severity of the lesion is directly related to the degree of subnormality of the readout. In cases of bilateral paralysis, the readouts on both sides are compared to predetermined normal values for a face response to determine the severity of the damage to either nerve. Similar results will also be obtained for other peripheral nerve-muscle systems.

Activation of a nerve with stimulus electrodes 44, 46 leads to the following sequence of events: (a) conduction of an electrical signal volley (compound action potential) down the nerve; (b) development of an electrical potential (EMG) in those muscle fibers controlled by the nerve, and (c) contraction and the generation of force by the muscle fibers. In the nerve conduction velocity test, the first event (the nerve compound action potential) is recorded and amplified. If the recording is displayed as a function of time on an oscilloscope screen and a sync signal is used to trigger the time base of the oscilloscope each time a stimulus is delivered, one can measure the time latency between a stimulus and response. The latency that is measured is the time it takes for the compound action potential to travel along the nerve from the stimulus electrodes to the recording electrodes. If a lesion develops in the nerve which causes a slowing of signal conduction, the latency of the response observed on the screen will become abnormally long. However, since any increase in latency of this event will produce comparable increases in latency of subsequent events further along in the sequence, one can record these later events and also determine the extent to which nerve conduction slowing had occurred because of a lesion. That is, one can record the evoked muscle EMG response, display it on the screen, and measure its latency to determine if nerve conduction slowing had occurred. Furthermore, the muscle force that is generated can be recorded with the subject device and displayed on the oscilloscope screen to obtain the same information regarding nerve conduction (by connecting trial force plug 35 to the oscilloscope; a stimulus sync signal is also provided for triggering the time base). By making appropriate connections to device 24, the sizes and latencies of force waveforms that are generated following each stimulus can be monitored and analyzed on an oscilloscope. Since the size of a waveform (or the waveform area) can indicate if nerve signal blocking from a lesion has occurred, device 24 is designed to give an automatic digital readout 32 of this information. This is probably the only information most physicians will need to make their diagnoses. However, having the option of monitoring waveforms on an oscilloscope and measuring response latencies may have importance in some clinical situations.

ADVANTAGES OF THE PREFERRED EMBODIMENT

Using the subject device 24, or a modification thereof depending upon the application, the method of evoked movement accelerometry as described has many distinct advantages over any other existing method for assessing peripheral nerve damage.

(1) The method is more sensitive than the others described, because it does not require the detection of small bioelectric signals through an insulating barrier—skin. Furthermore, while recording electrodes have fixed sensitivity, accelerometers can be constructed or bought commercially with almost any desired sensitivity. Using the accelerometer that has been constructed with the subject device 24, evoked accelerometry has generally ten times the sensitivity of evoked electromyography. The sensitivity is sufficiently high that minimal responses in a patient with severe nerve blockage can be measured without the aid of a signal averager.

(2) Since a signal averager is not required, the cost involved in using this method will be 1/10 to 1/5 that required in performing evoked electromyography. The low cost will afford many more physicians the opportunity to use this technique. Information important in patient care will thus be more readily obtained.

(3) The method is more accurate than the others. Since the method measures the movement of a whole body part, slight changes in the sensor position during repeated testing of a subject will not effect changes in the recorded response. As mentioned previously, slight changes in the recording electrode positions cause substantial changes in the recording when using the other methods. This leads to significant intertest error. In contrast to evoked electromyography, evoked accelerometry does not represent a "sampling technique". It can evaluate all the fibers in a peripheral nerve. It should be emphasized that accuracy in the evaluation of a peripheral nerve is important, so that patients do not undergo life threatening surgical operations unnecessarily.

(4) This method is much simpler than the others. It does not require the use of a signal averager or any other complicated peripheral equipment. It does not require the precise placement of three recording leads on the subject. Accelerometer sensor 20 is easy to affix to the subject and precision in placement is not required. After placing stimulus electrodes 44, 46 on the subject, the tester merely presses button 50 on the handheld unit and waits for the readout on LCD meter 32. The test can be performed by an untrained, inexperienced person. Since the unit is portable, it can be performed anywhere including at a patient's bedside.

(5) There is no risk of fatal electric shock with this method while there is with the others. Recording electrodes used in these other methods must make good electrical contact with the subject. Since the recording electrodes are connected to an AC powered component (amplifier), there is a risk of electric shock. In contrast, accelerometer sensor 20 does not make electrical contact to the subject and its leads 74 are not connected to an AC powered device, so there is no risk of electric shock.

SUMMARY OF THE INVENTION OF THE PREFERRED EMBODIMENT

The above-described system and method was developed for studying various regions of the nervous system that control muscular activity in humans and animals. The method utilizes a system which includes a small accelerometer sensor 20, stimulus electrodes 44, 46, and a portable device 24 containing circuits 26, 28, 30 for processing sensor data, generating stimuli, and timing both the extraction of sensor information and the delivery of stimuli. Sensor 20 measures the acceleration of a body part during movement. As long as the mass of the body part remains constant, the acceleration measured is also an index of the force which produces the movement. Sensor 20 is attached to a site on the body part through static suction of compartment 42. Since sensor 20 has negligible mass and is easy to attach, the device is versatile and can monitor movement of most muscles, extremities, or digits of the body depending upon the clinical or experimental condition being examined. In particular, the device can be used to investigate the neurological control of a specific body part during either voluntary or involuntary movements, or movements evoked by electrical stimulation of a peripheral nerve or region of the central nervous system.

Although the principal application is that of assessing the pathological status of a peripheral nerve, the device has many other applications (as explained supra in greater detail) including: evaluation of signal transmission blocking of a nerve or neuromuscular junction because of a disease or a chemical agent; intraoperative monitoring of the status of a peripheral nerve; intraoperative monitoring of the location of a peripheral nerve; studying the neural control of voluntary movement in man and animals; evaluation of the neural control of voluntary movement in patients; and evaluation of patients with involuntary tremors, such as occur in Parkinson's disease or with lesions of the cerebellum.

In some of these applications, the particular force parameter that is primarily of interest (e.g., threshold, latency, frequency) may differ from that in the principal application (i.e., force magnitude). The device has been designed with the flexibility to be interfaced with peripheral components, so that these parameters can also be monitored and analyzed. In some cases a direct readout of this information is displayed on device meter 32. Alternatively, force waveforms can be displayed on an oscilloscope or strip chart recorder for detailed analysis. Since sensor 20 can be placed anywhere on the body and can measure force along one, two or three axes of three-dimensional space, this method has a much broader scope of applications than methods employing force transducers. Force transducers measure differential forces between two sites on the body (e.g., across a joint) and must be constructed in a precise way for each application. As previously outlined, the subject method has the versatility of electromyography in evaluating neurological disorders and monitoring movement without its inherent limitations.

ADDITIONAL APPLICATIONS OF THE SUBJECT TECHNOLOGY

The following applications are further illustrative examples demonstrating the use of this method. The method as previously described basically includes measurement of acceleration of a body part along one, two or three axes of three dimensional space for the purpose of evaluating neurological function in man and animals.

Condition I: Movement evoked through stimulation of a peripheral nerve.

A. Evaluation of signal transmission blocking of a nerve or neuromuscular junction because of a disease or a chemical agent.

Blocking of nerve conduction by a chemical agent can be assessed using the same methodology as with a nerve lesion. The maximum integrated force that can be evoked during a minute's stimulation can be compared to normal values to determine the extent of chemical blocking.

Figure 9:
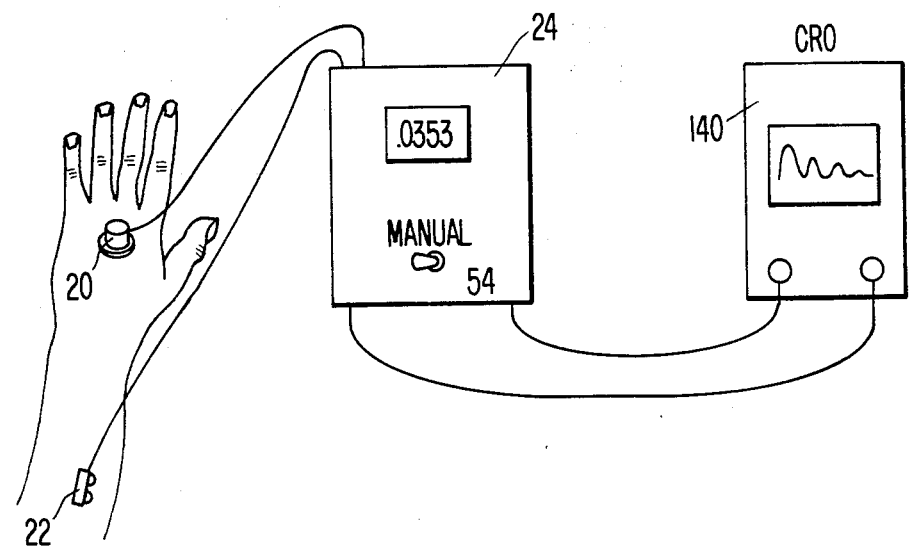
FIG. 9 is a block diagram of a second application of the invention of FIG. 1.

Blocking of a neuromuscular junction because of a disease or chemical can be assessed in a slightly different manner. Some diseases (e.g., *myasthenia gravis*) and some chemicals (succinyl choline) effect changes in the efficacy of transmission across junctions between nerve fiber terminals and their muscle fibers. Normally the force that can be evoked with repetitive stimulation of a nerve increases, and this is called post-tetanic potentiation. With certain types of diseases and chemical blocking agents, a decrease rather than an increase in evoked force is observed during repetitive stimulation. This is called post-tetanic depression and can provide a means for assessing neuromuscular blocking. In this application, as illustrated in FIG. 9, the trial BNC output of the device 24 is connected to a storage oscilloscope 140 or strip chart recorder. Nerve stimulation can be performed by flipping the "stim mode" switch 54 to the manual position. The decrement in evoked force that is observed over a prescribed number of stimuli (usually four) is noted and can give an estimate of the degree of neuromuscular blocking.

B. Intraoperative monitoring of the status of a peripheral nerve.

During surgical exposure of a peripheral nerve, this device 24 can be used to find sites on the nerve where damage has occurred and evaluate the severity of damage. The setup for this application is essentially the same as illustrated in FIG. 9 except that the nerve is exposed and bipolar wire or forceps electrodes are used to directly stimulate the nerve. Stimuli can be delivered to the exposed nerve at various spots and the response obtained at each site noted on the device meter or oscillosope 140. The response obtained at a given site can be compared to a control response obtained by stimulation of the nerve distal to the region of damage. Any subnormality in a response obtained at a site indicates the severity of nerve blocking at the site. The degree to which nerve damage has affected conduction speed at each site can also be evaluated by measuring response latencies on an oscilloscope 140.

C. Intraoperative monitoring of the location of a peripheral nerve.

Figure 10:
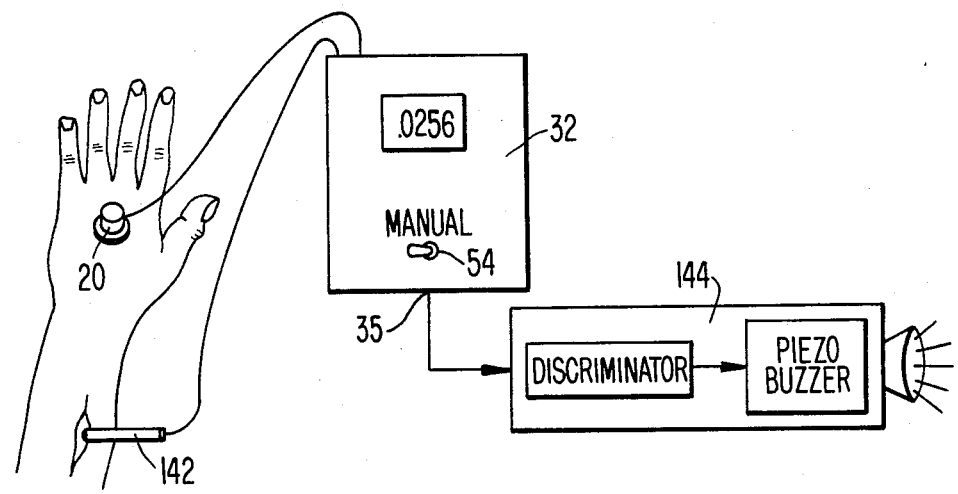
FIG. 10 is a block diagram of a third application.

In some instances, surgery is performed near a nerve but the nerve is not exposed. This device can be used to warn the surgeon if he is approaching too close to the nerve with a surgical instrument, as generally illustrated in FIG. 10. In this application stimuli can be delivered through the surgical instrument or probe 142. The sensor 20 is attached to the body part with an adhesive pad (for long term monitoring) and device 32 switched to "manual mode" for continuous generation of stimuli. The stimulus intensity is set to a level known to activate the nerve if instrument 142 serving as the electrode is brought within a prescribed distance of the nerve. If instrument 142 is close enough to activate the nerve, movement will be evoked and a readout of force will be displayed on the device meter, thereby warning the surgeon. Since an audible alarm would be a better warning signal, a small D.C. powered, discriminator-bell unit 144 can be plugged into the trial force output plug 35 to sound an alarm when a predetermined level of force is evoked. Thus, the readout on the meter or the audible alarm of unit 144 warns the surgeon if instrument 142 is too close to the nerve.

D. Studying the neural control of movements evoked by electrical stimulation of the central nervous system of normal humans, patients, and animals.

Condition II: Movement evoked voluntarily.

E. Studying the neural control of voluntary movement in man and animals.

If device 32 is switched into "manual mode" and the trial force output is connected to oscilloscope 140, force development can be monitored continuously in a human subject or animal performing voluntary motor tasks. This information can be correlated with, for example, invasive or noninvasive recordings from the nervous system to investigate the neural control of movement. The setup for this application is illustrated generally in FIG. 9, except that no stimulus is applied. Body part movement monitored on oscilloscope 140 is correlated with other recordings.

F. Studying the neural control of voluntary movement in patients.

Since force development of a muscle, extremity, or digit can be monitored with this device when connected to an external monitor such as an oscilloscope 140, abnormalities in the neural control of movement can be studied in patients. Lesions of various motor pathways can be assessed, including those controlling the limbs, trunk, and head. Lesions of other pathways, bearing an integral relationship to these motor pathways, can also be assessed for abnormalities. For example, angular acceleration of the head could be measured in a patient to determine the level at which abnormal eye movements (nyastagmus) occur as a test for "balance" or vestibular function. The setup for this application is illustrated in FIG. 9 except that no stimulus (22) is applied.

Condition III: Movement evoked involuntarily.

G. Evaluation of patients with involuntary tremors.

Figure 11:
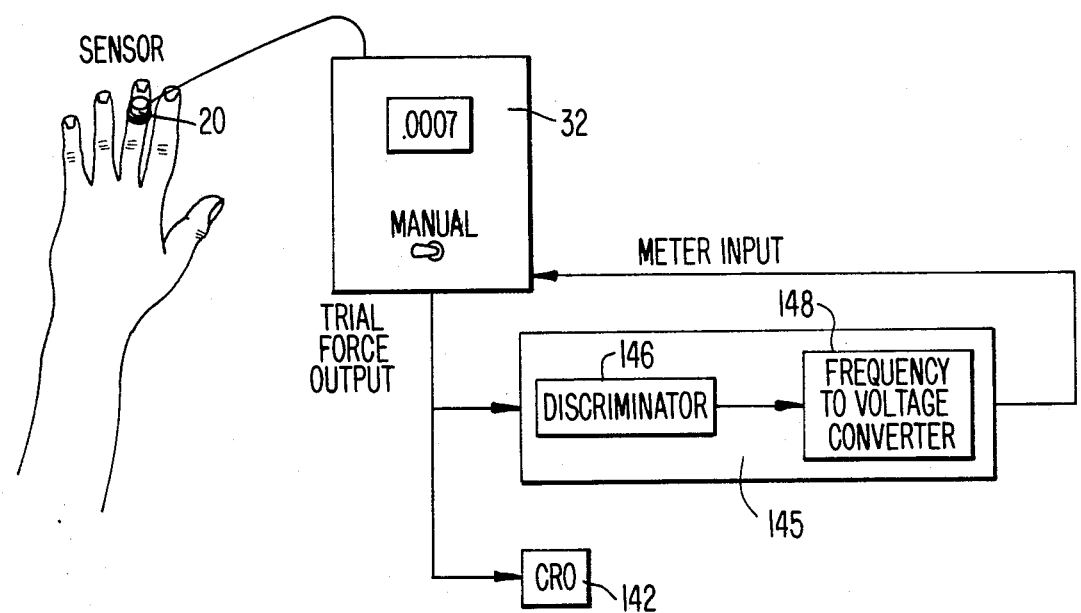
FIG. 11 is a block diagram of a fourth application.

In some diseases, disturbance of a motor pathway can result in repetitive involuntary movements or tremor, such as occurs in Parkinson's disease or cerebellar damage. In these patients determination of the frequency of the tremor can help assess the severity of the pathology. As illustrated in FIG. 11, if device 32 is connected to oscilloscope 142 and sensor 20 placed on a digit, the frequency of tremor in these patients can be evaluated. Alternatively, the tremor frequency can be displayed directly on the device meter by connecting the trial force plug 35 to a unit 145 containing a discriminator 146 and frequency to voltage converter 148. If discriminator 146 is set to a nominal level of force input, the output voltage of converter 148 will vary with tremor frequency. If the output of the converter is connected to the meter, this voltage can be displayed. The force waveforms are then studied on the CRO 142 or the frequency of the periodic movements (tremors) read out on the meter.

For this application, the setup is as shown in FIG. 9, except the stimulation is applied to the brain or spinal cord.

From the foregoing detailed description, it will be evident that there are a number of changes, adaptations, and modifications of the present invention which come within the province of those skilled in the art. However, it is intended that all such variations not departing from the spirit of the invention be considered as within the scope thereof as limited solely by the claims appended hereto.

We claim:

1. A system for evaluating motor nervous system function of the facial nerves of a subject comprising:
   an accelerometer sensing means for sensing the magnitude of acceleration of a part of the face of the subject along at least one axis of three-dimensional space,
   a monitoring means operatively associated with said sensing means for monitoring said sensed acceleration magnitudes,
   said monitoring means including a stimulating means for stimulating the facial nerves of the subject,
   said sensing means sensing the magnitude of the facial part acceleration evoked by said stimulating means, and
   said stimulating means including an electrode assembly and a positioning means for positioning said electrode assembly on the subject against the skin overlying the facial nerves below at least one of the subject's ears.

2. A system for evaluating nervous system function of a subject comprising:
   an accelerometer sensing means for sensing the actual acceleration of a body part of the subject along at least one axis of three-dimensional space,
   a monitoring means operatively associated with said sensing means for monitoring said sensed acceleration,
   said monitoring means measuring the magnitude of the acceleration and comparing said measured magnitude with a control magnitude to evaluate the subject's nervous system function,
   said control magnitude being the magnitude of acceleration of an evoked movement of another body part of the subject spaced from said body part, and
   said sensing means including a sensor which measures mechanical muscle energy of the subject and an attaching means for attaching said sensor to the body surface of the subject.

3. The system of claim 2 including,
   said control magnitude being the magnitude of acceleration of an evoked movement of another body part of the subject spaced from said body part,
   said body part being one side of the face of the subject, and
   said another body part being the side of the subject's face opposite said one side.

4. A system for the intraoperative monitoring of the location of a nerve in a patient comprising:
   a stimulating probe means for stimulating a motor nerve after an incision has been made in the patient and while the patient is under anesthesia during surgery to thereby evoke the movement of a body part of the patient,
   said stimulating probe means using a pulsatile current to stimulate the nerve,
   said current being rectangular pulses,
   an accelerometer sensing means for sensing the magnitude of the stimulated acceleration of said body part stimulated by said stimulating probe means in three-dimensional space,
   said sensing means directly monitoring the muscular response to said stimulated nerve, and
   an audible alarm advising means operatively connected to said sensing means for advising the surgeon when said stimulating probe means is within a set distance from the nerve.

5. The system of claim 4 including,
   said advising means including a visual meter read out.

6. The system of claim 4 including,
   said sensing means measuring the magnitude of the acceleration of said stimulated body part movement.

7. The system of claim 4 including,
   said audible alarm advising means being audible to the surgeon and by the strength of its alarm noise advising the surgeon whether he is getting closer to or farther from an unexposed nerve of the patient.

8. The system of claim 4 including,
   said advising means advising the surgeon by the change in the size of an audible advising response whether he is moving closer to or farther from said unexposed nerve.

9. A system for monitoring the status of an exposed, damaged nerve of a patient undergoing surgery comprising:
   a stimulating means for directly stimulating the exposed, damaged nerve at various locations thereon and thereby evoking the movement of a body part of the subject,
   an accelerometer sensing means for sensing the magnitude of the stimulated acceleration of said body part in three-dimensional space to evaluate nervous system function of the subject,
   a comparing means for comparing said sensed magnitude to a control magnitude, and
   a displaying means for displaying said magnitude of stimulated acceleration.

10. The system of claim 9 including,
    said comparing means including a measuring means for measuring response latencies, and
    a display means operatively connected to said measuring means for displaying said measured response latencies.

11. The system of claim 9 including,
    said stimulating means including a bipolar wire electrode.

12. The system of claim 9 including,
    said stimulating means including a bipolar forceps electrode.

13. The system of claim 9 including,
    said control magnitude being obtained by stimulating a nerve distal to the region of said damaged nerve and measuring the magnitude of the stimulated body part acceleration.

14. A method for evaluating motor nervous system function of a subject comprising:
    stimulating the nerve of the subject to evoke movement of a body part of the subject,
    measuring the magnitude of the actual evoked acceleration of the body part along at least one axis of three-dimensional space,
    said measuring including said body part being one side of the face of said subject,
    comparing said measured magnitude to a control magnitude to evaluate the function of the motor nervous system of the subject, and said comparing including stimulating the nerves of the subject on the side of his face opposite said one side and measuring the magnitude of the actual acceleration along at least one axis of three-dimensional space of the opposite face side evoked by said stimulating of said opposite face side to determine said control magnitude.

15. The method of claim 14 including,
said comparing including determining the blockage of signal transmission of a nerve by chemical agents.

16. The method of claim 14 including,
said comparing including determining the blockage of nerve conduction by nerve lesion.

17. The method of claim 14 including,
said measuring including said at least one axis comprising two perpendicular axes.

18. The method of claim 14 including,
said measuring including said at least one axis comprising three mutually perpendicular axes.

19. The method of claim 14 including, said opposite face side being unparalyzed.

20. A system for evaluating motor nervous system function of a subject comprising:
an accelerometer sensing means for sensing the actual linear acceleration of a body part of the subject along at least one axis of three-dimensional space of the stationary external world,
a monitoring means operatively associated with said sensing means for monitoring the magnitude of said sensed accelerations to evaluate the function of the subject's motor nervous system,
said monitoring means including a selecting means for selecting the time interval over which said monitoring means operates,
a stimulating means for stimulating the motor nerves of the subject, and
said monitoring means monitoring the magnitude of the body part acceleration evoked by said stimulating means.

21. The system of claim 20 including,
said at least one axis comprising two axes of three-dimensional space.

22. The system of claim 20 including,
said at least one axis comprising three axes of three-dimensional space.

23. The system of claim 20 including,
said monitoring means including a displaying means for displaying the monitored values.

24. The system of claim 20 including,
said monitoring means including a selecting means for selecting the time interval over which said monitoring means operates.

25. The system of claim 20 including,
said monitoring means including a measuring means for measuring the latency of force response following nerve stimulation by said stimulating means.

26. The system of claim 20 including,
said stimulating means including a stimulus electrode assembly, and
said sensing means including an accelerometer sensor for measuring the body part movement evoked by said stimulus electrode assembly.

27. The system of claim 20 including,
said sensing means sensing the evoked movement of a body part evoked by said stimulating means.

28. The system of claim 20 including,
said stimulating means stimulating the brain or spinal cord of the subject.

29. The system of claim 20 including,
said monitoring means determining the degree of damage to a part of the subject's motor nervous system.

30. The system of claim 20 including,
said accelerometer sensing means comprising a piezoresistive accelerometer.

31. A system for evaluating motor nervous system function of a subject comprising:
an accelerometer sensing means for sensing the actual acceleration of a body part of the subject along at least one axis of three-dimensional space of the stationary external world,
a monitoring means operatively associated with said sensing means for monitoring the magnitude of said sensed acceleration to evaluate the function of the subject's motor nervous system,
said sensing means including a sensor housing, a flexible cantilever filament attached at one end to said housing, a weight attached to the other end of said filament, a distorting means capable of being distorted and attached to said filament, said distorting means being caused to distort and the resistance thereof to be altered by the movement of said housing caused by said body part, and an observing means for observing said altered resistance, and
an attaching means for attaching said sensor housing to the subject.

32. The system of claim 31 including,
said attaching means comprising a static suction means, and
said static suction means including a generating means remote to said sensing means for generating a suction force, and a suction tubing connecting said generating means to said sensing means.

33. The system of claim 32 including, said generating means being a spring-loaded syringe.

34. The system of claim 31 including,
said attaching means being adapted to attach said sensor housing to generally all body parts of the subject.

35. A system for evaluating motor nervous system function of a subject comprising:
an accelerometer sensing means for sensing the actual acceleration of a body part of the subject along at least one axis of three-dimensional space of the stationary external world,
a monitoring means operatively associated with said sensing means for monitoring the magnitude of said sensed acceleration,
said sensing means sensing the magnitude of the acceleration serving as an index of the force of said movement,
said monitoring means monitoring the magnitude of the force of said movements to evaluate the function of the subject's motor nervous system, and
said monitoring means monitoring the maximum magnitude of the time integral of said force occurring over a testing period.

36. A system for evaluating motor nervous system function of a subject comprising:
an accelerometer sensing means for sensing the actual acceleration of a body part of the subject along at least one axis of three-dimensional space of the stationary external world, and a monitoring means operatively associated with said sensing means for monitoring the magnitude of said sensed acceleration, said monitoring means monitoring force development over a continuous range in the subject who is performing voluntary motor tasks and correlating the resulting information with recordings from the nervous system to investigate the neural control of movement of the subject, and said monitoring means including a displaying means for displaying the body part acceleration sensed by said sensing means as a function of time and over said continuous range.

37. The system of claim 36 including, said displaying means comprising an oscilloscope.

38. A system for evaluating motor nervous system function of a subject comprising:

a stimulating means for stimulating the motor nervous system of the subject to thereby evoke movement of at least one body part of the subject, an accelerometer sensing means for sensing the actual linear acceleration of the body part evoked by said stimulating means along at least one axis of three-dimensional space of the stationary external world, a monitoring means operatively connected to said sensing means for monitoring the magnitude of said sensed acceleration to evaluate the function of the subject's motor nervous system, and said monitoring means calculating the integral of the force detected by said sensing means over time.

39. A system for evaluating motor nervous system function of a subject comprising:

an accelerometer sensing means for sensing the actual acceleration of a body part of the subject along at least one axis of three-dimensional space of the stationary external world, a monitoring means operatively associated with said sensing means for monitoring the magnitude of said sensed acceleration, said monitoring means including a comparing means for comparing said acceleration magnitude to a normal value to evaluate the function of the subject's motor nervous system, and said comparing means expressing said magnitude as a percentage of said normal value.

40. A method for evaluating nervous system function of a subject comprising:

stimulating the nerve of the subject to evoke movement of a body part of the subject, measuring the magnitude of the actual evoked acceleration of the body part along at least one axis of three-dimensional space, comparing said measured magnitude to a control magnitude to evaluate the function of the nervous system of the subject, said comparing including monitoring the location of an unexposed peripheral nerve during surgery.

41. The method of claim 40 including, said comparing including evaluating the function of the subject's motor nervous system.

42. A method for evaluating nervous system function of a subject comprising:

stimulating the nerve of the subject to evoke movement of a body part of the subject, measuring the magnitude of the actual evoked acceleration of the body part along at least one axis of three-dimensional space, comparing said measured magnitude to a control magnitude to evaluate the function of the nervous system of the subject, said comparing including locating the sites on the damaged nerve where damage has occurred, and said comparing further including evaluating the severity of the damage to said damaged nerve at said sites.

43. A method for evaluating nervous system function of a subject comprising:

stimulating an unexposed nerve of the subject to evoke movement of a body part of the subject, measuring the magnitude of the actual evoked acceleration of the body part along at least one axis of three-dimensional space, comparing said measured magnitude to a control magnitude to evaluate the function of the nervous system of the subject, said comparing including intraoperative monitoring of the location of said unexposed nerve, and said intraoperative monitoring including alerting the surgeon when his surgical instrument gets too close to said unexposed nerve.

44. A system for the intraoperative monitoring of the location of a nerve in a patient comprising:

a stimulating probe means for stimulating an intact nondamaged motor nerve after an incision has been made in the patient and while the patient is under anesthesia during surgery to thereby evoke the movement of a body part of the patient, an accelerometer sensing means for sensing the magnitude of the stimulated acceleration of said body part stimulated by said stimulating probe means in three-dimensional space, and an audible alarm advising means operatively connected to said sensing means for advising the surgeon when said stimulating probe means is within a set distance from the nerve.

45. A system for the intraoperative monitoring of the location of a nerve in a patient comprising:

a stimulating probe means for stimulating an intact nondamaged motor nerve after an incision has been made in the patient and while the patient is under anesthesia during surgery to thereby evoke the movement of a body part of the patient, an accelerometer sensing means for sensing the magnitude of the stimulated acceleration of said body part stimulated by said stimulating probe means in three-dimensional space, an audible alarm advising means operatively connected to said sensing means for advising the surgeon when said stimulating probe means is within a set distance from the nerve, and said sensing means giving an objective measurement to the surgeon of the size of the body part response to the stimulation of the patient's motor nerve by said stimulating probe means.

46. A system for evaluating motor nervous system function of a subject comprising:

an accelerometer sensing means for sensing the actual linear acceleration of a body part of the subject along at least one axis of three-dimensional space of the stationary external world, a monitoring means operatively associated with said sensing means for monitoring the magnitude of said sensed accelerations to evaluate the function of the subject's motor nervous system, a stimulating means for stimulating the motor nerves of the subject, said monitoring means including a sensor circuit for processing sensor information from said sensing means, said stimulating means including a stimulus circuit for delivering stimuli to the motor nerve controlling said body part, and said monitoring means further including a timing circuit for timing both the delivery of the stimuli by said stimulus circuit and the extraction of processed sensor information from said sensor circuit.

47. The system of claim 46 including, said monitoring means including an evaluating means for evaluating the function of the subject's motor nervous system.

48. A system for evaluating motor nervous system function of a subject comprising:

an accelerometer sensing means for sensing the actual linear acceleration of a body part of the subject along at least one axis of three-dimensional space of the stationary external world, a monitoring means operatively associated with said sensing means for monitoring the magnitude of said sensed accelerations to evaluate the function of the subject's motor nervous system, a stimulating means for stimulating the motor nerves of the subject, and said stimulating means activating the subject's facial nerve root as it exits his skull below and behind his ear lobe.

49. A system for evaluating motor nervous system function of a subject comprising:

an accelerometer sensing means for sensing the actual linear acceleration of a body part of the subject along at least one axis of three-dimensional space of the stationary external world, a monitoring means operatively associated with said sensing means for monitoring the magnitude of said sensed accelerations to evaluate the function of the subject's motor nervous system, a stimulating means for stimulating the motor nerves of the subject, and said monitoring means monitoring the magnitude of the movement electrically evoked by said stimulating means for assessing the severity of damage to the subject's motor nervous system.

50. A system for evaluating motor nervous system function of a subject comprising:

an accelerometer sensing means for sensing the actual linear acceleration of a body part of the subject along at least one axis of three-dimensional space of the stationary external world, said body part being a small patch of skin generally a few millimeters in diameter, a monitoring means operatively associated with said sensing means for monitoring the magnitude of said sensed accelerations to evaluate the function of the subject's motor nervous system, and a stimulating means for stimulating the motor nerves of the subject.

51. A system for evaluating motor nervous system function of a subject comprising:

an accelerometer sensing means for sensing the actual linear acceleration of a body part of the subject along at least one axis of three-dimensional space of the stationary external world, a monitoring means operatively associated with said sensing means for monitoring the magnitude of said sensed accelerations to evaluate the function of the subject's motor nervous system, a stimulating means for stimulating the motor nerves of the subject, and said monitoring means monitoring the magnitude of the movement electrically evoked by said stimulating means for assessing the severity of damage to the subject's motor nervous system.

* * * * *